United States Patent
Zhu et al.

(10) Patent No.: US 7,127,291 B2
(45) Date of Patent: Oct. 24, 2006

(54) CORONARY SINUS LEAD WITH THERMAL SENSOR AND METHOD THEREFOR

(75) Inventors: Qingsheng Zhu, Little Canada, MN (US); Jeffrey E. Stahmann, Ramsey, MN (US); John Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 425 days.

(21) Appl. No.: 10/087,377

(22) Filed: Mar. 1, 2002

(65) Prior Publication Data

US 2003/0167081 A1    Sep. 4, 2003

(51) Int. Cl.
*A61N 1/00* (2006.01)
(52) U.S. Cl. ........................................ 607/21; 607/122
(58) Field of Classification Search ................ 607/122, 607/21, 17, 18, 119; 600/549
See application file for complete search history.

(56) References Cited

U.S. PATENT DOCUMENTS

| | | | |
|---|---|---|---|
| 4,240,441 A | 12/1980 | Khalil | 128/692 |
| 4,688,573 A * | 8/1987 | Alt | 607/21 |
| 5,174,299 A | 12/1992 | Nelson | 128/692 |
| 5,174,303 A | 12/1992 | Schroeppel | 128/786 |
| 5,306,252 A | 4/1994 | Yutori et al. | 604/164 |
| 5,358,519 A | 10/1994 | Grandjean | 623/3 |
| 5,376,106 A | 12/1994 | Stahmann et al. | 607/18 |
| 5,904,708 A | 5/1999 | Goedeke | 607/18 |
| 6,033,398 A | 3/2000 | Farley et al. | 606/27 |
| 6,042,580 A | 3/2000 | Simpson | 606/32 |
| 6,049,737 A | 4/2000 | Simpson et al. | 607/119 |
| 6,179,832 B1 | 1/2001 | Jones et al. | 606/32 |
| 6,309,385 B1 | 10/2001 | Simpson | 606/32 |
| 6,312,425 B1 | 11/2001 | Simpson et al. | 606/32 |
| 6,391,024 B1 | 5/2002 | Sun et al. | 606/34 |
| 2003/0125774 A1* | 7/2003 | Salo | 607/21 |

* cited by examiner

*Primary Examiner*—Jeffrey Jastrzab
*Assistant Examiner*—Alyssa M. Alter
(74) *Attorney, Agent, or Firm*—Schwegman, Lundberg, Woessner, & Kluth, P.A.

(57) ABSTRACT

A lead system is provided including a coronary sinus lead extending from a proximal end to a distal end, where the lead includes at least one thermal sensor, or optionally, a thermistor. The thermal sensor is positionable within a coronary sinus of a heart when the coronary sinus lead is implanted in the heart to measure the temperature of a myocardium. The method includes coupling at least one thermal sensor with the implantable lead, including coupling a first thermal sensor and a second thermal sensor with the lead, placing the implantable lead and at least one thermal sensor within a coronary sinus of a heart and positioning the first thermal sensor within the coronary sinus, and positioning the second thermal sensor within a right atrium of a heart. The method further includes coupling the implantable lead with the implantable electrical stimulation source, and measuring a myocardium temperature.

20 Claims, 2 Drawing Sheets

CORONARY SINUS LEAD WITH THERMAL SENSOR AND METHOD THEREFOR

TECHNICAL FIELD

The present invention relates generally to leads for an implantable electrical stimulator. More particularly, it pertains to a coronary sinus lead with thermal sensor.

BACKGROUND

Core body temperature of a congestive heart failure patient exhibits patterns of behavior under certain circumstances. For instance, the core temperature of a congestive heart failure patient tends to decrease during exercise, primarily due to the circulatory inadequacies associated with this condition. Shellock (J Appl Physiol 1985 February; 58(2): 400–8) studied core temperatures (pulmonary arterial blood), femoral vein, muscle, and skin temperatures in eight patients with severe heart failure performing maximal upright incremental bicycle exercise to 50 W. A normal group of four individuals was exercised for comparison. In the heart-failure patients, the core temperature was 36.95+/−0.37 degrees C. at rest, and decreased to 36.59+/−0.40 degrees C. at 25 W of exercise. At 50 W of exercise, the temperatures were 36.57+/−0.40 degrees C. In contrast, the resting core temperature in the normal subjects was 37.28+/−0.34 degrees C. At 25 W of exercise, the core temperature in the normal subjects was the same as the resting core temperature. At 50 W of exercise, the temperature of the normal subjects increased to 37.50+/−0.32 degrees C.

Currently, leads are used, for example, to measure a core temperature of a body where the thermal sensor is placed in the right ventricle to measure a mix of the blood temperature, as discussed in U.S. Pat. No. 4,688,573, issued on Aug. 25, 1987. However, the core temperature of a body, or blood which flows through the right ventricle, involves an average temperature of many locations. For instance, blood from within the right ventricle is blood collected from the brain, kidney, lymph system as well as other locations within the body, resulting in a temperature which is an average of all of these locations. Collecting readings of average temperatures such as the above may not provide accurate information regarding what is occurring only within the heart, or the effectiveness of the heart.

Accordingly, what is needed is a more accurate way to monitor the effectiveness of a heart.

SUMMARY

A lead system is provided herein which more accurately monitors the effectiveness of a heart. The lead system includes a coronary sinus lead extending from a proximal end to a distal end, where the proximal end of the coronary sinus lead is optionally coupled with an electrical stimulation source. One or more conductors are disposed within the coronary sinus lead. The lead includes at least one thermal sensor, or optionally, a thermistor. The thermal sensor is positionable within a coronary sinus of a heart when the coronary sinus lead is implanted in the heart to measure the temperature of a myocardium.

Several options for the lead system are as follows. For instance, in one option, the lead includes at least one electrode, such as a pacing electrode. In another option, the at least one thermal sensor includes a first thermal sensor and a second thermal sensor, and optionally the first thermal sensor is positionable in the coronary sinus and the second thermal sensor is positionable in a right atrium of the heart when the first thermal sensor is positioned in the coronary sinus.

In another embodiment, a lead system includes an over-the-wire coronary sinus lead including a lead body extending from a proximal end to a distal end. The over-the-wire coronary sinus lead includes at least one thermal sensor coupled thereto, and at least one thermal sensor coupled with at least one conductor. Optionally, one or more thermistors are coupled with the over-the-wire coronary sinus lead. The lead further optionally includes at least one pacing electrode, and means for measuring temperature of the myocardium that includes at least one thermal sensor positionable within a coronary sinus of a heart when the over-the-wire coronary sinus lead is implanted in the heart.

Several options for the lead system are as follows. For instance, in one option, the system further includes a second thermal sensor coupled with at least one conductor, and the second thermal sensor is positionable within a right atrium of the heart when the at least one thermal sensor is positioned in the coronary sinus of the heart. In another option, the lead system further includes a means for measuring a core temperature. In yet another option, the proximal end of the over-the-wire coronary sinus lead is coupled with an implantable electrical stimulation source.

In another embodiment, a method is provided which includes providing an implantable lead and an implantable electrical stimulation source, coupling at least one thermal sensor with the implantable lead, coupling at least one electrode with a portion of the implantable lead, placing the implantable lead and at least one thermal sensor within a coronary sinus of a heart, and measuring a myocardium temperature from the thermal sensor within the coronary sinus of the heart.

Several variations for the method are as follows. For instance, in one option, coupling at least one thermal sensor includes coupling a first thermal sensor and a second thermal sensor with the lead. In another option, the method further includes positioning the first thermal sensor within the coronary sinus, and positioning the second thermal sensor within a right atrium of a heart, and optionally further includes measuring a first temperature within the coronary sinus, and a second temperature in the right atrium. Still further, the method further optionally includes measuring a difference between the first temperature and the second temperature, and pacing the heart in light of the difference. In yet another option, the method includes measuring temperature changes in the coronary sinus, and optionally pacing the heart with the lead, and adjusting delivery of pacing signals in light of temperature changes in the coronary sinus, or optionally using the temperature changes in the coronary sinus as an indication of a change in the functional status of the heart.

In yet another embodiment, a method includes providing an implantable lead and an implantable electrical stimulation source, coupling at least one electrode with the implantable lead, coupling at least one thermal sensor with the implantable lead, including coupling a first thermal sensor and a second thermal sensor with the lead, placing the implantable lead and at least one thermal sensor within a coronary sinus of a heart and positioning the first thermal sensor within the coronary sinus, and positioning the second thermal sensor within a right atrium of a heart. The method further includes coupling the implantable lead with the implantable electrical stimulation source, and measuring a myocardium temperature.

Several options for the method are as follows. For instance, in one option, the method further includes monitoring temperature changes within the coronary sinus and temperature changes within the right atrium. In another option, the method further includes providing pacing pulses to the electrode when a decrease in temperature in the first thermal sensor is detected. Optionally, the method further includes monitoring a rate of temperature change in the coronary sinus, and monitoring a rate of temperature change in the right atrium. The method further includes, in one option, determining whether the rate of temperature change in the coronary sinus is greater than the rate of temperature change in the right atrium. Optionally, the method further includes providing pacing pulses to the at least one electrode if the rate of temperature change in the coronary sinus is greater than the rate of temperature change in the right atrium, and if the temperature in the coronary sinus is less than the temperature of the right atrium.

The lead system and method provides for the myocardium temperature to be more closely and accurately monitored. More precise data of the myocardium temperature can be developed and/or monitored, where the data is not skewed by variations of temperatures occurring in distal body parts or vasculature. The therapy given in light of the data collection is more responsive to actual conditions of the myocardium, where the temperature of the coronary sinus comes from the temperature of the myocardium, and it is well insulated from the rest of the body. This is in contrast with temperatures monitored from the right ventricle, where the right ventricle temperatures represents an average temperature from several locations within the body. Thus, monitoring the temperature of the coronary sinus monitors the temperature of the myocardium, and work done by the heart is accurately measured by the temperature of the coronary sinus and myocardium. Data comparison with temperatures from the coronary sinus and the right atrium allows for determining whether heart failure is present or the degree of heart failure is changing.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
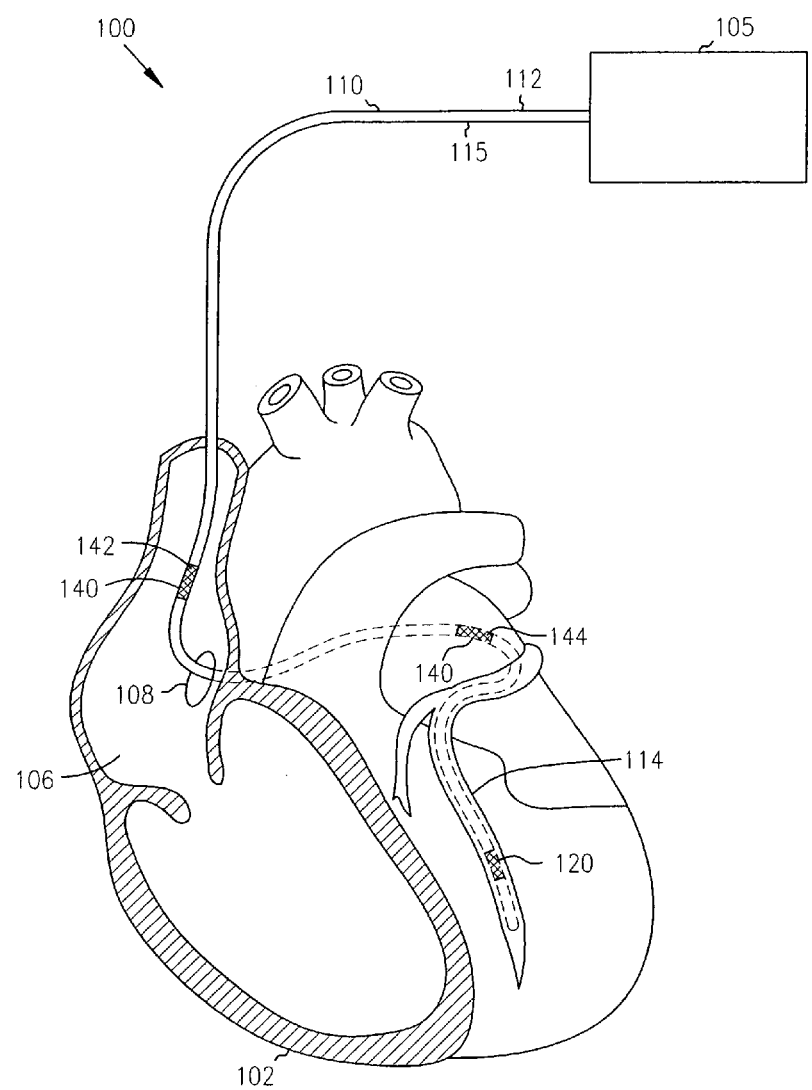
FIG. 1 illustrates a lead system constructed in accordance with one embodiment.

A lead is provided which measures the temperature of the myocardium. Referring to FIG. 1, the lead 110 is part of a system 100 which includes an implantable electrical source 105, such as a pulse generator. The implantable electrical source 105 provides, for example, electrical pulses that are transmitted by the lead 110 to tissue, as further described below. The implantable electrical source 105 contains electronics to sense various electrical signals of the heart 102 and also produce current pulses for delivery to the heart 102. The implantable electrical source 105 is implanted pectorally, abdominally, or elsewhere within the patient.

The lead 110 is, in one option, a coronary sinus lead that extends from a proximal end 112 to a distal end 114, where the proximal end 112 is electrically coupled with the implantable electrical source 105. In another option, the lead 110 comprises an over-the-wire coronary sinus lead. The lead 110 optionally includes at least one electrode 120. The at least one electrode 120, in one option, is disposed at the distal end 114 of the lead 110. The at least one electrode 120 optionally comprises a pacing electrode, which provides pulses to tissue, such as a portion of the heart 102, as further discussed below. In another option, the lead 110 includes a defibrillation electrode.

The lead 110 includes a lead body 115, for instance a flexible lead body 115, and at least one elongate conductor contained within the lead body 115. The at least one electrode 120 is electrically coupled with the elongate conductor. Optionally, the elongate conductor comprises a coiled conductor and defines a lumen therein and thereby is adapted to receive a stiffening stylet that extends through the length of the lead 110.

The stylet is used to stiffen the lead 110, and is manipulated to facilitate the insertion of the lead 110 into and through a vein to advance the distal end 114 of the lead 110 into, for example, the coronary sinus 108 of the heart 102, or a right atrium 106 of the heart 102. Optionally, a stylet knob is coupled with the stylet for rotating the stylet, advancing the conductor into tissue of the heart, and for manipulating the lead 110. Alternatively, the elongate conductor comprises other forms of conductors, such as a cable conductor.

The lead body 115 includes an elongate body formed of, for example, at least one polymer such as a medical grade silicone rubber for translumenal insertion and access within a living organism such as a patient. In one option, the lead body 115 is tubular and has an outer diameter that is small enough for translumenal insertion into the coronary sinus 108.

The lead 110, in one option, is implanted within the heart such that the lead extends into the coronary sinus 108. The lead 110 further includes one or more thermal sensors 140 coupled thereto. The one or more thermal sensors 140 is coupled with one of the conductors, and sends information from its location within the coronary sinus 108 to the implantable electrical source 105, or another data collection source, such as an external source. Optionally, at least one of the one or more thermal sensors 140 comprises a thermistor, where thermistors are passive semiconductors which produce resistance values dependent on temperature. The thermistor is sized small enough for suitable use on the lead, and can be configured for lower power consumption.

In one option, at least one of the one or more thermal sensors 140 is positioned within the coronary sinus 108 of the heart 102. Positioning the thermal sensor within the coronary sinus 108 allows for the temperature of the myocardium to be more directly measured, monitored, and reacted to as further described below. In another option, the lead 110 includes multiple thermal sensors 140, including a first thermal sensor 142 and a second thermal sensor 144. The first thermal sensor 142 and the second thermal sensor 144 are positioned on the lead 110 such that the first thermal sensor 142 is positioned within the right atrium 106 while the second thermal sensor 144 is positioned within the coronary sinus 108. Having the ability to monitor the temperature within the coronary sinus 108 provides information regarding the myocardium, and compare it to the temperature within the atrium. Furthermore, the second thermal sensor 144 allows for the core temperature of a patient to be monitored.

Figure 2:
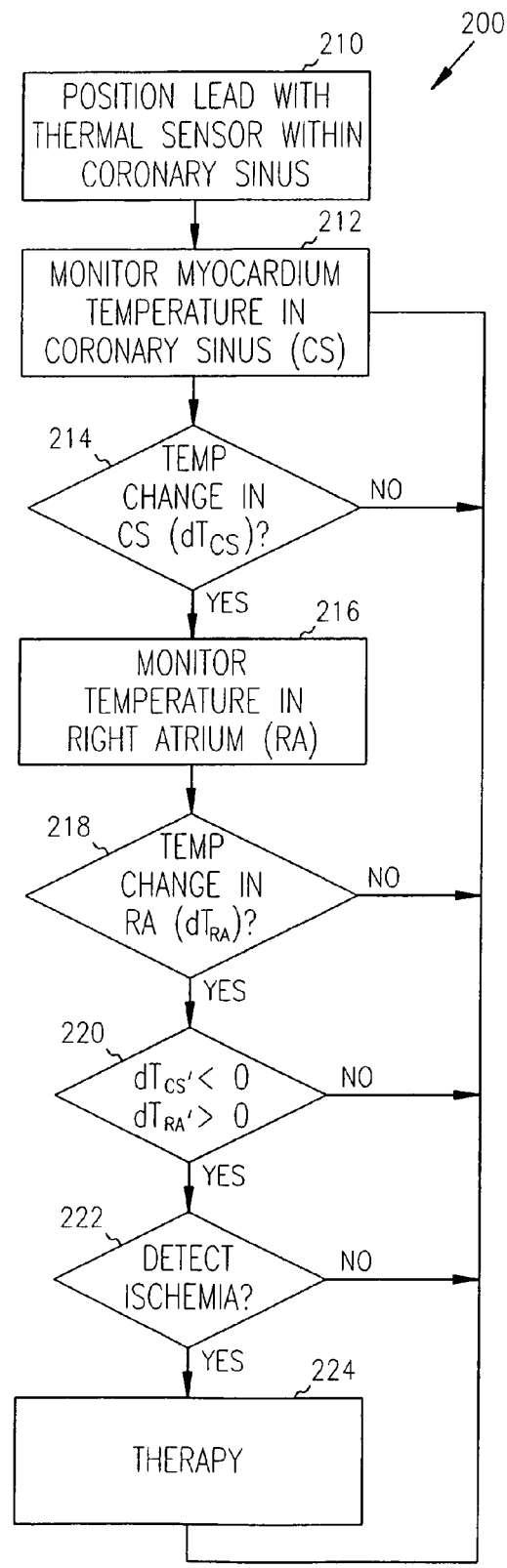
FIG. 2 is a block diagram illustrating a method in accordance with one embodiment.

FIG. 2 illustrates a block diagram of a method 200. The method includes the above-described embodiments of the lead, and the variations are combinable to form further variations of the method and/or lead. During use of the lead, the lead is implanted within the heart, for example using an over-the-wire technique, and/or using a stylet. The lead is moved through the vasculature of a patient and the distal end of the lead, in one option, is positioned within the coronary sinus, such that one of the thermal sensors is positioned within the coronary sinus 210. In another option, at least one of the thermal sensors is disposed along an intermediate portion of the lead, and the thermal sensor is positioned within the coronary sinus.

Within the coronary sinus, the myocardium temperature is monitored 212 and information regarding the temperature readings is sent back to the electrical source and optionally stored. In one option, temperature change in the coronary sinus is used as an indicator of change in the functional status of the heart. As heart failure progresses, the body's core temperature will trend lower over time, indicating the patient is becoming more ill. The temperature of the blood in the coronary sinus is a measure of the work being performed by the heart. As the heart does work, it generates "waste heat" since it is not 100% efficient. This waste heat is transferred to the circulating blood returning in the coronary sinus. Ischemia, for example, impairs the heart's ability to do work. As the work rate of the heart falls, the amount of waste heat falls, leading to a drop in temperature in the myocardium and ultimately in the blood returning via the coronary sinus.

The temperature change in the coronary sinus and/or change in functional status of the heart is reported to the physician so that changes in therapy can occur to improve the patient's condition. The report to the physician occurs, in one option, when a patient's device is coupled with a programmer, for example, directly with hard wires, over a phone line, or over the internet.

In another option, a second thermal sensor is coupled with the lead, and the lead is positioned within the heart such that the first thermal sensor is positioned within the coronary sinus, and the second thermal sensor is positioned within the right atrium. Within the right atrium, the second thermal sensor monitors the temperature of the right atrium 216, as further discussed below.

In one option, the lead takes a first temperature reading and a consecutive second temperature reading within the coronary sinus. Optionally, additional consecutive temperature readings within the coronary sinus are taken and stored. The first temperature reading and the second temperature reading are compared to one another to determine whether the temperature of the coronary sinus is changing, 214 ($dT_{CS}$). If no change in temperature occurs, the temperature of the coronary sinus is continually monitored, 212. If a change in the temperature occurs, one or more of several options is chosen. For instance, the change in temperature is analyzed for a decrease or increase in temperature, and it is further determined whether a decrease or increase in temperature is appropriate, for example, if the patient is exercising. Exercise or work is monitored, in one option, by an activity sensor (e.g. an accelerometer to sense patient motion) and/or a minute ventilation sensor to sense increased respiration, indicating increased metabolic demand.

Furthermore, in another option, if a change in the temperature occurs in the coronary sinus, the right atrium is monitored for a change in temperature 216. If temperature readings within the right atrium indicate that the temperature of the right atrium is changing ($dT_{RA}$) 218, the rate of the temperature change in the coronary sinus is determined ($dT_{CS}'$), and the rate of the temperature change in the right atrium is determined ($dT_{RA}'$).

The rate of the temperature change in the coronary sinus ($dT_{CS}'$) is compared to the rate of the temperature change in the right atrium ($dT_{RA}'$), 220. This is done to determine if the amount of work being performed by the myocardium is appropriate to provide the needs of the body. Furthermore, if it is determined that the rate of temperature change in the coronary sinus ($dT_{CS}'$) is different than the rate of temperature change in the right atrium ($dT_{RA}'$), it may signal an imbalance in the amount of work being done by the heart.

For instance, if the temperature in the right atrium is increasing, and the temperature in the coronary sinus is decreasing, it may indicate decreased cardiac output despite increased metabolic demand. If it is determined that the temperature of the myocardium is not changing or decreasing during exercise, a possible ischemic condition is present, 222, and appropriate therapy is applied to the patient, 224.

The above-described apparatus and method provides for the myocardium temperature to be more closely and accurately monitored. More precise data of the myocardium temperature can be developed, monitored, where the data is not skewed by variations of temperatures occurring in distal body parts or vasculature. The therapy given in light of the data collection is more responsive to actual conditions of the myocardium, where the temperature of the coronary sinus comes from the temperature of the myocardium, and it is well insulated from the rest of the body. This is in contrast with temperatures monitored from the right ventricle, where the right ventricle temperatures represents an average temperature from several locations within the body. Thus, monitoring the temperature of the coronary sinus monitors the temperature of the myocardium, and work done by the heart is accurately measured by the temperature of the coronary sinus and myocardium. Data comparison with temperatures from the coronary sinus and the right atrium allows for another way of determining whether heart failure is present or the degree of heart failure is changing.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A method comprising:
   providing an implantable lead and an implantable electrical stimulation source;
   coupling at least a first and a second thermal sensor with the implantable lead;
   placing the implantable lead within a coronary sinus of a heart, including positioning the first thermal sensor within the coronary sinus, and positioning the second thermal sensor within a right atrium of the heart;
   measuring a myocardium temperature from the first thermal sensor within the coronary sinus of the heart; and
   measuring a temperature change within the coronary sinus.

2. The method as recited in claim 1, further comprising measuring a first temperature within the coronary sinus, and a second temperature within the right atrium.

3. The method as recited in claim 2, further comprising measuring a difference between the first temperature and the second temperature, and pacing the heart in light of the difference.

4. The method as recited in claim 1, further comprising pacing the heart, and adjusting delivery of pacing signals in light of the temperature change within the coronary sinus.

5. The method as recited in claim 1, further comprising using the temperature change within the coronary sinus as an indicator of a change in the functional status of the heart.

6. A method comprising:
   providing an implantable lead and an implantable electrical stimulation source;
   coupling at least one electrode with the implantable lead;
   coupling at least one thermal sensor with the implantable lead, including coupling a first thermal sensor and a second thermal sensor with the lead;
   placing the implantable lead within a coronary sinus of a heart and positioning the first thermal sensor within the coronary sinus, and positioning the second thermal sensor within a right atrium of a heart;
   coupling the implantable lead with the implantable electrical stimulation source; and
   measuring a myocardium temperature.

7. The method as recited in claim 6, further comprising monitoring temperature changes within the coronary sinus and temperature changes within the right atrium.

8. The method as recited in claim 6, further comprising providing pacing pulses to the electrode when a decrease in temperature in the first thermal sensor is detected.

9. The method as recited in claim 6, further comprising monitoring a rate of temperature change in the coronary sinus, and monitoring a rate of temperature change in the right atrium.

10. The method as recited in claim 9, further comprising determining whether the rate of temperature change in the coronary sinus is greater than the rate of temperature change in the right atrium.

11. The method as recited in claim 10, further comprising providing pacing pulses to the at least one electrode if the rate of temperature change in the coronary sinus is greater than the rate of temperature change in the right atrium, and if the temperature in the coronary sinus is less than the temperature of the right atrium.

12. The method as recited in claim 6, further comprising monitoring temperature changes in the coronary sinus and using the temperature changes in the coronary sinus as an indicator of a change in the functional status of the heart.

13. A method comprising:
    providing an over the wire implantable lead and an implantable electrical stimulation source;
    coupling at least a first and a second thermal sensor with the implantable lead;
    coupling at least one electrode with a portion of the implantable lead;
    placing the implantable lead within a coronary sinus of a heart;
    positioning the first thermal sensor within the coronary sinus, and positioning the second thermal sensor within a right atrium of the heart;
    measuring a myocardium temperature from the first thermal sensor within the coronary sinus of the heart; and
    pacing the heart with the lead, and adjusting delivery of pacing signals using the myocardium temperature measured within the coronary sinus.

14. The method as recited in claim 13, further comprising monitoring a rate of temperature change in the coronary sinus, and monitoring a rate of temperature change in the right atrium.

15. The method as recited in claim 13, further comprising measuring a difference between a first temperature within the coronary sinus and a second temperature in the right atrium, and pacing the heart in light of the difference.

16. The method as recited in claim 13, further comprising monitoring a temperature change in the coronary sinus and using the temperature change in the coronary sinus as an indicator of a change in the functional status of the heart.

17. A method comprising:
 providing an over the wire implantable lead and an implantable electrical stimulation source;
 coupling at least one thermal sensor with the implantable lead;
 coupling at least one electrode with a portion of the implantable lead;
 placing the implantable lead within a coronary sinus of a heart;
 positioning one or more of the at least one thermal sensor within the coronary sinus; measuring a myocardium temperature from the one or more thermal sensor within the coronary sinus of the heart; and
 pacing the heart with the lead, including providing pacing pulses to the at least one electrode when a decrease in temperature in the one or more thermal sensor within the coronary sinus is detected.

18. The method as recited in claim 17, further comprising monitoring a temperature change within the coronary sinus, and using the temperature change within the coronary sinus as an indicator of a change in the functional status of the heart.

19. The method as recited in claim 17, further comprising positioning one or more of the at least one thermal sensor within a right atrium of the heart and measuring a temperature within the right atrium.

20. The method as recited in claim 19, further comprising measuring a difference between the temperature within the coronary sinus and the temperature within the right atrium, and pacing the heart in light of the difference.

\* \* \* \* \*